(12) United States Patent
Foo et al.

(10) Patent No.: US 7,691,423 B2
(45) Date of Patent: Apr. 6, 2010

(54) METHOD OF TREATING INFLAMMATION DISORDERS USING EXTRACTS OF PASSION FRUIT

(75) Inventors: Lai Yeap Foo, Lower Hutt (NZ); Yinrong Lu, Lower Hutt (NZ); Ronald Ross Watson, Tucson, AZ (US)

(73) Assignees: Industrial Research Limited, Parnell, Auckland (NZ); Southwest Scientific Editing, Tucson, AZ (US)

( * ) Notice: Subject to any disclaimer, the term of this patent is extended or adjusted under 35 U.S.C. 154(b) by 0 days.

(21) Appl. No.: 12/178,390

(22) Filed: Jul. 23, 2008

(65) Prior Publication Data

US 2009/0022832 A1      Jan. 22, 2009

Related U.S. Application Data

(63) Continuation-in-part of application No. 11/417,721, filed on May 4, 2006, now abandoned, which is a continuation-in-part of application No. 11/098,101, filed on Apr. 4, 2005, now Pat. No. 7,390,517.

(51) Int. Cl.
*A61K 36/00*      (2006.01)

(52) U.S. Cl. ................... 424/777; 424/775; 424/725

(58) Field of Classification Search ............... None
See application file for complete search history.

(56) References Cited

U.S. PATENT DOCUMENTS

| | | | |
|---|---|---|---|
| 6,210,738 B1 * | 4/2001 | Chen | 426/597 |
| 6,544,581 B1 * | 4/2003 | Shrikhande et al. | 426/655 |
| 6,555,142 B1 * | 4/2003 | Green | 424/725 |
| 6,605,306 B1 * | 8/2003 | Green | 424/733 |
| 7,157,109 B2 * | 1/2007 | Kipfer | 426/599 |
| 2002/0055471 A1 | 5/2002 | Bailey et al. | |

FOREIGN PATENT DOCUMENTS

| | | | |
|---|---|---|---|
| JP | 2001668494 | * | 4/2001 |
| JP | 2003307350 | | 3/2005 |
| JP | 2005350433 | * | 12/2005 |
| JP | 2009073767 | * | 4/2009 |

OTHER PUBLICATIONS

Mohamed et al. Pertankia J. Trop. Agric. Soc., 1994, vol. 17, No. 3, pp. 219-227.*
DK Natural Health—Encyclopedia of Herbal Medicine. 2000. 2nd ed., pp. 290-291, Dorling Kindersley Limited, London.*
Kidoy et al. J. Food Composition and Analysis. 1997. vol. 10, pp. 49-54.*
Pruthi et al. J. Food Sci. 1961. vol. 26, pp. 385-388.*
Chassagne et al. J. Agric. Food Chem. 1996. vol. 44, No. 12, pp. 3817-3820.*
Dhawan, K., Dhawan, S., Sharma, A., "*Passiflora*: a review update", Journal of Ethno-Pharmacology, 94, 2004, 1-23.
Zibadi, S. & Watson, R.R., "Passion Fruit: Composition, Efficacy and Safety", Evid Based Integrative Med, 2004, 183-87.
Dhawan, K., Kumark, S., Sharma, A., "Compartive Biological acitivity study on *Passiflora incarnata* and *P. edulis*" Fitoterapia, 72, 2001, 698-702.
Lue, S.J., Deacidification of passion fruit juice by ultrafiltration and ion-exchange processes. International Journal of Food Science and Technology. 1989, vol. 24, pp. 395-401.
Vera Calle, E., Deacidification of the clarified passion fruit juice (*P. edulis f. flavicarpa*). Desalination. 2002, vol. 149, pp. 357-361.
Vera, E., Comparison of different methods for deacidification of clarified passion fruit juice. Journal of Food Engineering. 2003. vol. 50. pp. 361-367.
Vera, E., Comparison between different ion exchange resins for the deacidification of passion fruit juice. Journal of Food Engineering. 2003. vol. 57, pp. 199-207.
Ichimura, T., Yamanaka, A., Ichiba, T., et al., "Antihpertensive Effect of an Extract of *Passiflora edulis* Rind in Spontaneously Hypertensive Rats", Biosci. Bitechnol. Biochem, vol. 70, No. 3, 2006, 718-721.
Frode T S et al: "Anti-inflammatory effects of *Passiflora edulis* Sims on the mouse model of pleurisy induced by carrageenan," Clinical Chemistry, vol. 50, No. 6, suppl. S, part 2, Jun. 2004, pp. A36-A37, XP002445818 & 56th Annual Meeting of the American Association for Clinical Chemistry (AACC); Los Angeles, CA, USA; Jul. 25-29, 2004.
Frode T S et al: "Species of *Passiflora* inhibit markers of inflammation in a marine model;" Clinical Chemistry, vol. 51, no Supple. 6, 2005, p. A208, XP001536631 & Annual Meeting of the American-Association-for-Clinical-Chemistry; Orlando, FL, USA; Jul. 24-28, 2005.
Sherma Zibadi et al: Passion Fruit (*Passiflora edulis*). Composition Efficacy and Safety; Evidence-Based Integrative Medicine, ADIS International, Auckland, NZ; vol. 1, No. 3, 2004, pp. 183-187 XP007902754.
Kidoy, Linda et al.: "Anthocyanins in fruits of *Passiflora edulis* and *P. suberosa*" Journal of Food Composition and Analysis, vol. 10, No 1 1997, pp. 49-54, XP-2535196.
S. Zibadi: "Passion fruit (*Passiflora edulis*). Composition, efficay and safety" Evid Base Integrative Med, vol. 1, No. 3, 2004, pp. 183-187, SP002535204.
Dhawan Kamaldeep et al.: "*Passiflora*: a review update" Journal of Ethnopharmacology, vol. 94, No. 1, Sep. 2004, pp. 1-23, SP002535205.
Mohamed, et al.: Antimicrobial activity of some tropical fruit wastes (guava, starfruit, banana, papaya, passionfruit, langsat, duku, rambutan and rambai). Pertanika Jouranl of Tropical Agricultural Science. 1994, vol. 17, No. 3, pp. 219-227.
Chevallier, A. DK: Natural Health. In: Encyclopedia of Herbal Medicine. 2000, 2nd Ed., pp. 290-391. Dorling Kindersley Limited (London).

* cited by examiner

*Primary Examiner*—Christopher R. Tate
(74) *Attorney, Agent, or Firm*—Kent A. Herink; Emily E. Harris

(57) ABSTRACT

An extract of the skin or peel of passion fruit is prepared. The extract has the effect of ameliorating the symptoms of inflammation disorders, including asthma and osteoarthritis, in mammals, including humans, when administered in an effective amount.

9 Claims, 15 Drawing Sheets

*Significant by Mann-Whitney, P=0.009

METHOD OF TREATING INFLAMMATION DISORDERS USING EXTRACTS OF PASSION FRUIT

RELATED APPLICATIONS

This application is a continuation-in-part of U.S. application Ser. No. 11/417,721, filed May 4, 2006, now abandoned which is a continuation-in-part of U.S. application Ser. No. 11/098,101, filed Apr. 4, 2005 now U.S. Pat. No. 7,390,517.

BACKGROUND OF THE INVENTION

The invention relates generally to botanical extracts and, more specifically, to extracts of passion fruit (*Passiflora* sp.), including particularly extracts of the skin of passion fruit, and the use of the extracts for food, nutraceutical, and medical applications.

Hypertension, or a blood pressure higher than 140/90 mm Hg, is the most common risk factor for cardiovascular and cerebrovascular morbidity and mortality. In the United States, high blood pressure is responsible for 40,000 deaths annually, while being the most modifiable risk factor for stroke. Hypertension affects about one in four adults, or almost 50 million people in the United States.

A Framingham study showed that as people aged from 30 to 65 years, their blood pressure increased an average 20 mm Hg systolic and 10 mm Hg diastolic pressure, with systolic blood pressure continuing to rise up to age 90.

While higher blood pressure increases the likelihood of a cardiovascular event, hypertension is not often well controlled and too few patients are adequately treated. Epidemiologic studies predict that reduction of the systemic blood pressure by the amount usually achieved in major clinical trials could reduce cerebrovascular events by 42% and cardiac events by 24%

Hypertension is frequently treated non-specifically, resulting in a large number of minor side effects, and a relatively high rate of non- or inadequate treatment. Thus, the search for new treatments for hypertension remains ongoing.

Therapies derived from natural products are well known. It has been established that certain flavonoids have a beneficial effect on hypertension. For example, a bark extract from the French maritime pine (*Pinus pinaster*), which contains a mixture of flavonoids, decreases systolic blood pressure when taken orally by mildly hypertensive patients.

Nitric oxide is an important molecular regulator of blood pressure. Nitric oxide is a potent vasodilator. It inhibits platelet activation, limits leukocyte adhesion to the endothelium, and regulates myocardiocontractility. Synthesis of nitric oxide catalyzed by nitric oxide synthase (NOS) occurs in the vascular endothelium while the production of nitric oxide involving inducible nitric oxide synthase (iNOS) is associated with immune function. However, small amounts of nitric oxide produced by another NOS, epithelial nitric oxide synthase (eNOS), have a cytoprotective effect and vasodilation action on the cardiovascular system.

Peroxynitrite is a potentially damaging oxidant, formed from nitric oxide ($NO+O_2ONOO$). Peroxynitrite can give rise to lipid peroxidation, protein nitration, DNA single-strand breakage, and guanidine nitration.

It has been shown that the flavonoids quercetin and kaempferol inhibit NOLA-dependent spontaneous aortic ring contraction in spontaneously hypertensive rat (SHR) cells in vitro. NOLA is a nitric oxide synthase inhibitor. Large dose acetylcholine-induced vascular contraction can also be inhibited by antioxidative flavonoids such as quercetin, kaempferol, rutin, and esculetin. Inhibition of vascular smooth muscle contraction should lead to lower blood pressure.

In addition, the effects of flavonoids on immune function are controversial. Catechin enhances proliferation of lymphocytes and antibody production, while it exerts an inhibitory effect at high concentration. Some studies show that flavonoids enhance NK cell activity, while other studies show that flavonoids have no effect. Quercetin seems to inhibit non-specific immunological responses and exerts an anti-inflammatory action.

Asthma is a very common disease, affecting 4-5% of the population of the United States with incidence increasing rapidly. It is recognized as comprising a chronic, eosinophilic bronchitis and mediator-driven inflammatory process in the lungs. These agents produce potent bronchoconstriction, increased endothelial membrane permeability leading to airway edema, and enhanced secretion of thick, viscous mucus (Wenzel S E. Arachidonic acid metabolites: Mediators of inflammation in asthma. Pharmacotherapy 1997; 17(1 Pt2): 3S-12S). A widespread narrowing of the air passages manifests asthma. This may be relieved spontaneously or as a result of therapy, and is defined clinically by paroxysms of dyspnea, cough, and wheezing. Asthma is an episodic disease: acute exacerbations are interspersed with symptom-free periods. Oxidants, organic dust, airborne allergens, chemical substances, cold air, and virus infections can trigger asthma attacks. Most attacks are short-lived, lasting minutes to hours, and clinically the patient recovers completely afterwards.

Although asthma is primarily a disease of airways, virtually all aspects of pulmonary function are compromised during an acute attack. When a patient presents for therapy, forced vital capacity (FVC) tends to be less than 50% of normal. The 1-second forced expiratory volume ($FEV_1$) averages 30% or less than that of healthy people, and the maximum and minimum mid-expiratory flow rates are reduced to 20% or less than expected. In acutely ill patients, the residual volume (RV) frequently approaches 400% of normal and functional residual capacity doubles. The patients usually report that the attack has clinically ended when the RV has fallen to 200% of its predicted value and the $FEV_1$ reaches 50% of the predicted value (American Thoracic Society: Lung function testing: Selection of reference values and interpretative strategies. Am Rev Respir Dis 1991; 144:1202-1218).

Asthma diagnosis is established by demonstrating reversible airway obstruction. Reversibility is traditionally defined as a 15% or greater increase in $FEV_1$ after 2 puffs of a β-adrenergic agonist. Once the diagnosis is confirmed, the course of the illness and the effectiveness of therapy can be monitored by measuring peak expiratory flow rate at home or $FEV_1$ in the laboratory or both. Successful asthma treatment is accomplished with the use of a β-agonist for the early stage and reduction of inflammation with anti-inflammatory agents such as glucocorticoids (which decrease airway hyper-responsiveness) for the late stage.

More than 15 million Americans suffer from rheumatoid and osteoarthritis. The most common source of adult disability is due to osteoarthritis of the knee. Studies have documented radiological knee osteoarthritis and symptomatic osteoarthritis in 12% and 6%, respectively, of women aged 45-64. It has also been reported that the age-and-sex standardized incidence rate for knee osteoarthritis is approximately 240 of 100,000 persons per year.

Although osteoarthritis is not considered an inflammatory disease, mediators classically associated with inflammation perpetuate cartilage damage that ensues from repeated mechanical injury. Cartilage destruction, an important pathological feature and a major cause of joint dysfunction, is mediated by two distinct pathways: Intrinsic, in which chondrocytes are responsible for the degradation of the extracellular matrix; and extrinsic, wherein cells and tissues other than chondrocytes, such as inflamed synovium, pannus tissue, and inflammatory cells affect the extra cellular matrix via synovial fluids.

It has been shown that Matrix metalloproteinases (MMPs), major proteolytic enzymes involved in extracellular matrix turnover, are expressed in osteoarthritic cartilage and contribute to tissue damage. Another suspected mediator of tissue damage is overproduction of nitric oxide (NO), a major catabolic factor produced by chondrocytes in response to proinflammatory cytokines such as IL-1$\beta$ and TNF-$\alpha$. Non-steroidal anti-inflammatory drugs (NSAIDs) are the most commonly used medications for arthritis, but are associated clinically with significant complications including non-ulcer dyspepsia, symptomatic gastric and duodenal ulcers, ulcer hemorrhages and perforations. Their economic impact includes 100,000 hospitalizations annually, costing $1.6 billion with 17,000 deaths. The complications of NSAIDs have increased with the aging of the American population and heightened use of aspirin for cardioprophylaxis. Accordingly, there is an increasing need to develop effective and safe treatment to minimize the adverse events in patients with osteoarthritis.

Passion fruit (*Passiflora edulis*) is a subtropical or tropical plant with a vigorous climbing character, growing to 20 ft. The purple passion fruit is native from southern Brazil through Paraguay to northern Argentina. Its fruit is nearly round or ovoid, 1.5 to 3 inches wide, with a tough, smooth and waxy rind.

In a search for bioactive constituents of passion fruit, it has now surprisingly been found that a passion fruit extract has an ameliorating effect on inflammation disorders. Inflammation, particularly chronic inflammation, has been implicated in cancer, hypertension, allergy, diabetes, chronic skin disorders, and autoimmune diseases such as lupus and multiple sclerosis. Passion fruit extract lowers systolic blood pressure in spontaneously hypertensive rats (SHR), and decreases nitric oxide production from iNOS, thus improving endothelial dysfunction in SHR. It is therefore also envisaged that the passion fruit extract will exhibit antioxidant properties. Passion fruit extract decreases the severity of symptoms of asthma, including wheezing, coughing, shortness of breath, and reduced expiratory functions. Passion fruit extract decreases the severity of osteoarthritis, including pain, stiffness and physical function.

It is therefore an object of the invention to provide an extract of passion fruit which exhibits therapeutic effects against hypertension and diseases associated with hypertension, asthma, osteoarthritis, and which is hepatoprotective, or at least to provide a useful choice.

SUMMARY OF THE INVENTION

In a first aspect, the invention provides a method of lowering blood pressure in a mammal comprising administering an effective amount of a passion fruit extract to the mammal.

In another aspect, the invention provides a method of preventing or treating a disease or disorder in a mammal where it is desirable to lower blood pressure comprising administering an effective amount of a passion fruit extract to the mammal.

There is also provided a method of lowering serum nitric oxide levels in a mammal comprising administering an effective amount of a passion fruit extract to the mammal.

The invention further provides a method of treating a disease or disorder related to liver function in a mammal comprising administering an effective amount of a passion fruit extract to the mammal.

The invention therefore provides a method of treating hypertension as well as any other disease or disorder associated with elevated blood pressure. The invention further provides a method of hepatoprotection in a mammal, as well as a method of treating any disease or disorder related to liver function.

The invention further provides the use of a passion fruit extract as an antioxidant to inhibit damage from free radicals, to reduce serum lipid peroxidation and to preserve healthy tissue antioxidant vitamin levels.

The invention also provides the use of passion fruit extract as a treatment for the symptoms of inflammation disorders.

The invention further provides the use of passion fruit extract as a treatment for the symptoms of inflammation disorders of asthma and osteoarthritis.

The passion fruit extract of the invention includes, but is not limited to, one or more of the group selected from quercetin, cyanidin glycoside, catechin, epicatechin, luteolin, phenylpyruvic acid, the novel edulilic acid isolated and described herein, and any glycoside thereof.

Preferably, the passion fruit extract is prepared by a process including the following steps: preferably, cutting the passion fruit into pieces to increase the surface area; contacting the pieces of passion fruit with water to give an aqueous extract and a solid residue; separating the aqueous extract from the solid residue; contacting the aqueous extract with a polymeric matrix to adsorb one or more components of the extract onto the matrix; washing the matrix with water; and eluting the one or more components from the matrix with an organic solvent or mixture of organic solvents.

Optionally, the skin of the passion fruit is removed from the flesh and used in the extraction process.

It is preferred that the organic solvent is methanol, ethanol, isopropyl alcohol, 1-propanol, or acetone.

The invention also provides a composition containing the passion fruit extract.

The composition may be a food or food product. The composition may also be a dietary supplement, such as a nutraceutical or other nutritional composition.

Alternatively, the composition may be a pharmaceutical composition comprising the extract described above, admixed with one or more pharmaceutically acceptable excipients.

In a further aspect, the invention provides the use of a passion fruit skin extract as a nutraceutical, such as a dietary supplement, or as an active ingredient in the preparation of medical or functional foods and beverages.

DETAILED DESCRIPTION OF PREFERRED EMBODIMENTS

Figure 1A:
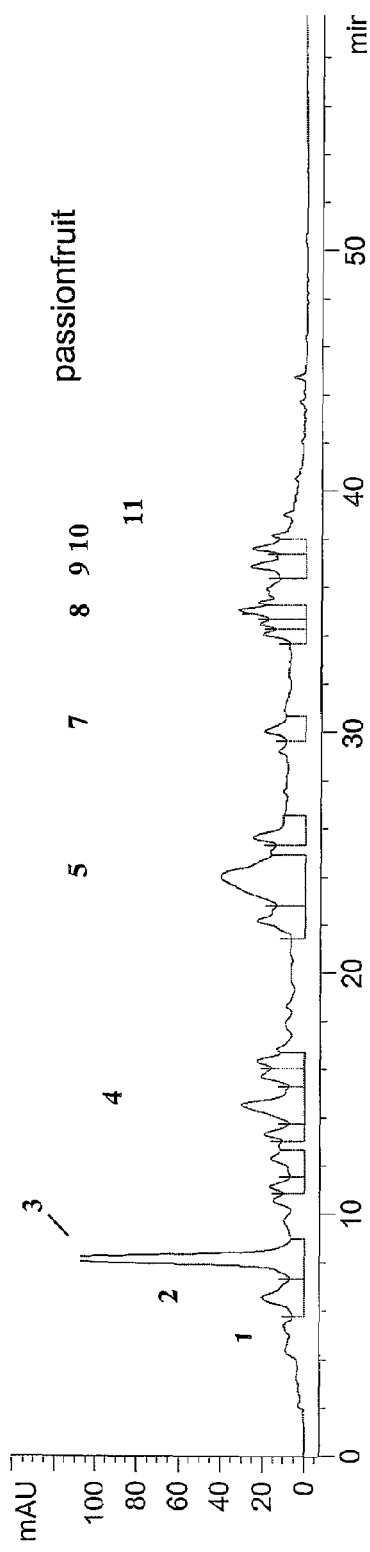
FIGS. 1*a-c* are HPLC traces of the extract of passion fruit made according to the present invention.
Figure 1B:
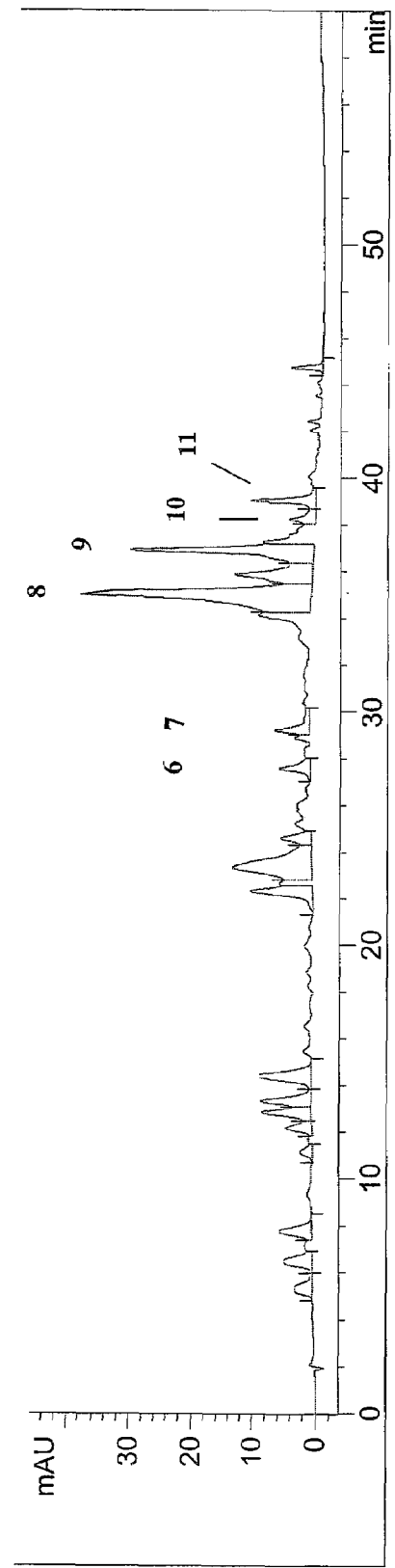
Figure 1C:
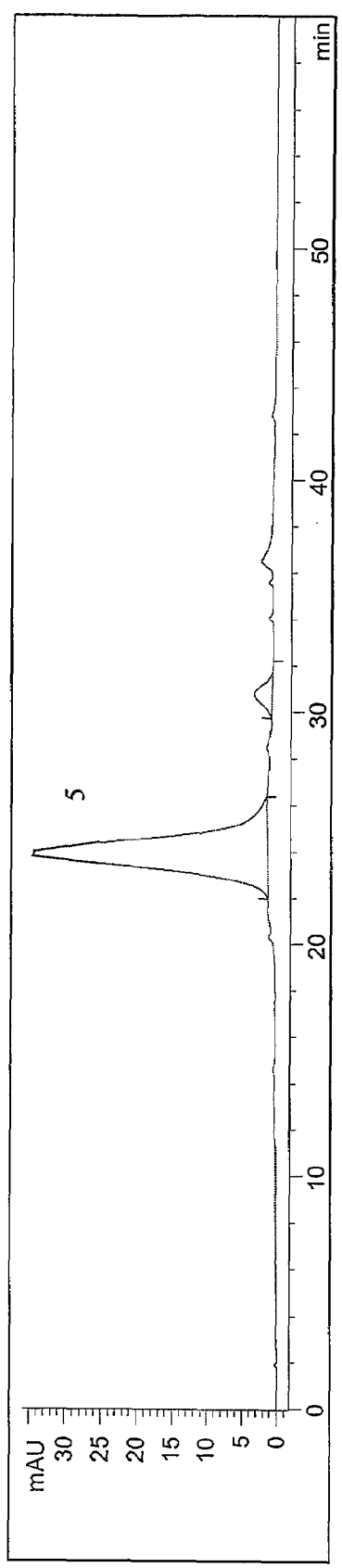

As described herein, "passion fruit" means generally the fruit including both the skin and the edible pulp. The term "passion fruit skin" is used to mean the remaining part of the fruit after the edible pulp inside has been removed. The terms "passion fruit extract", "PFP", and "PFP extract" are used to mean the extract of passion fruit prepared according to methods described in the examples of the preferred embodiments of the present invention. HPLC analysis indicates that the passion fruit extract contains a number of flavonoids, including quercetin, quercetin galactoside, quercetin glucoside, luteolin, luteolin glucoside, cyanidin-3-glucosides, catechin and epicatechin. (FIG. 1).

The flavonoid and cyanidin components of the extract inhibit superoxide formation and nitric oxide production from iNOS, thus improving endothelial dysfunction and lowering blood pressure. Quercetin has been shown to inhibit iNOS mRNA and the production of nitric oxide.

Human essential hypertension is characterized by impaired endothelium-dependent vasodilation, caused by oxidative stress. The extract of the invention has anti-hypertensive effects. In addition, the flavonoid components of the extract lower blood pressure, inhibit oxidation of LDL, and inhibit platelet aggregation, thereby exerting a cardiovascular protecting action. It is noted that the components of the extract include quercetin, a compound know to have antihypertensive activity, but the amount contained in the extract is less than between about 1 and 5% and is not sufficient to substantially account for the antihypertensive activities of the extract. Indeed, none of the previously known constituents of the extract are present in quantities sufficient to provide the observed effects alone.

It is also envisaged, based on the in vitro data, that the extract will have antioxidant properties.

Figure 2:
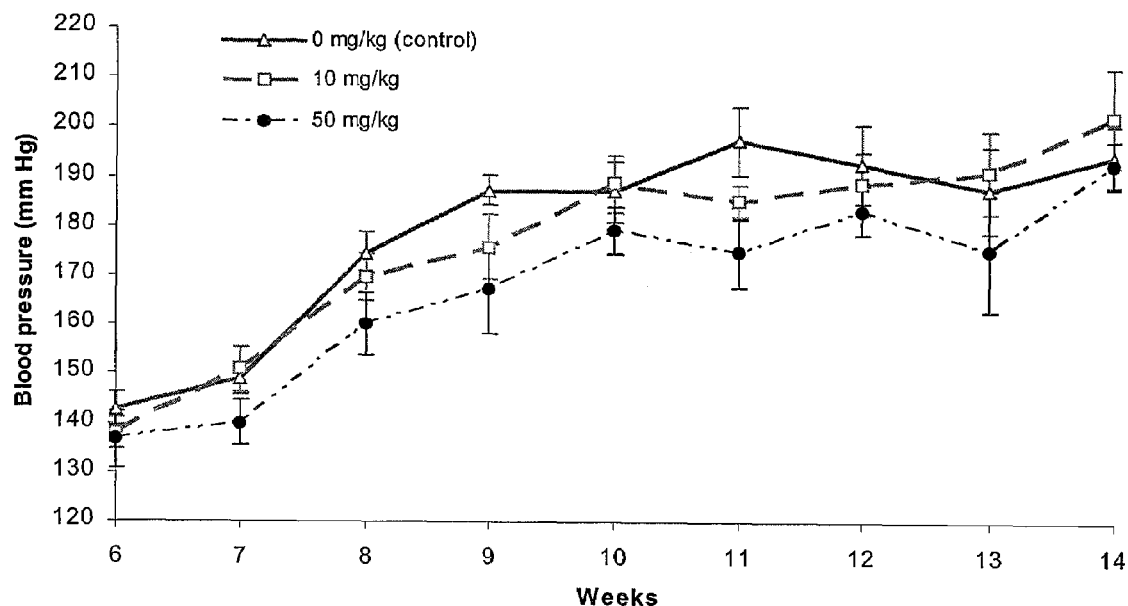
FIG. 2 is a diagrammatical representation of data showing the reduction in blood pressure in a group of spontaneously hypertensive rats administered the extract of passion fruit.

In studies with spontaneously hypertensive rats (SHR), the applicants found that diets supplemented with 50 mg/kg of the extract lowered blood pressure in SHR, retarding their normal increase in blood pressure due to aging. Systolic blood pressure was 12.3 mm Hg lower in rats fed 50 mg/kg of the extract, compared with a control group (P<0.01) (FIG. 2).

Figure 3:
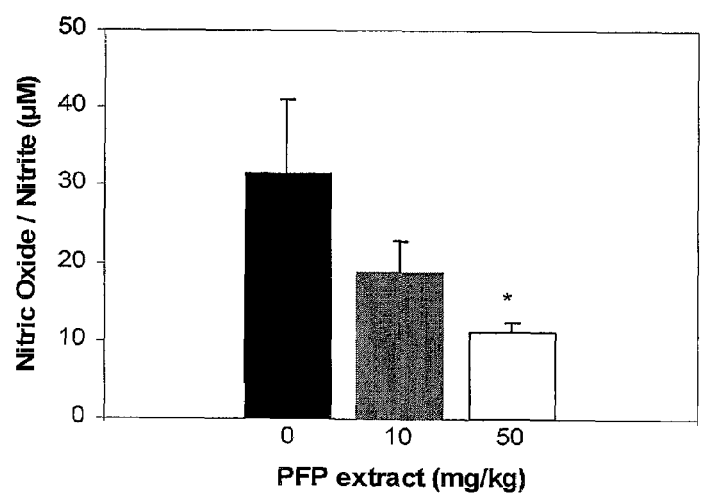
FIG. 3 is a diagrammatical representation of data showing the reduction in serum nitric oxide levels in a group of rats administered the extract of passion fruit.

Furthermore, nitric oxide concentration was 18.82 µmol/L in rats fed with 10 mg/kg of the extract, 40% lower than that in rats fed no extract. The nitric oxide concentration was 11.07 µmol/L in rats fed with 50 mg/kg of the extract, 65% lower than that in rats fed no extract (FIG. 3). This will prevent the overproduction of nitric oxide and its subsequent reaction to form peroxynitrite which is detrimental to the cardiovascular system.

The applicants have also found, in rat liver studies, that the passion fruit extract is hepatoprotective. Precision-cut rat liver slices were incubated with 20 µg/ml of passion fruit extract. At 9 and 24 hours incubation, potassium levels in the slices, an index of viability, were not significantly different from control slices.

The extract was then incubated with precision-cut rat liver slices in the presence or absence of 1 mM chloroform, a hepatotoxicant. At 6 hours incubation and at 9 hours incubation the passion fruit extract showed significant hepatoprotection against chloroform injury. No toxicity of the extract was found in this study.

Figure 4A:
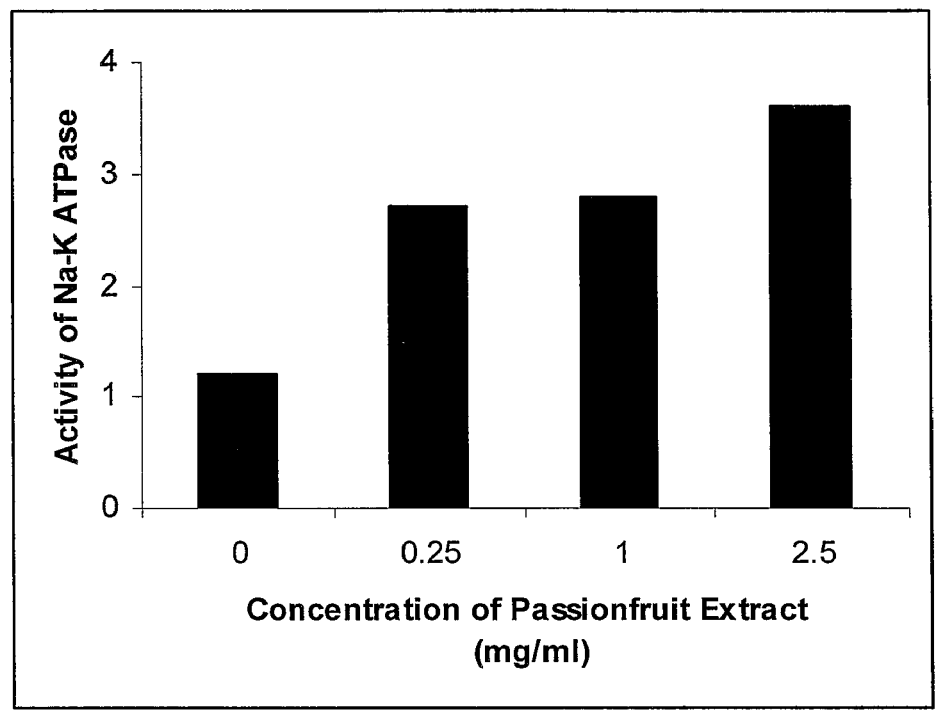
FIGS. 4*a* and 4*b* are diagrammatical representations of data showing the in vivo increase in activity of Na—K ATPase and Ca ATPase, respectively, by the extract of passion fruit.
Figure 4B:
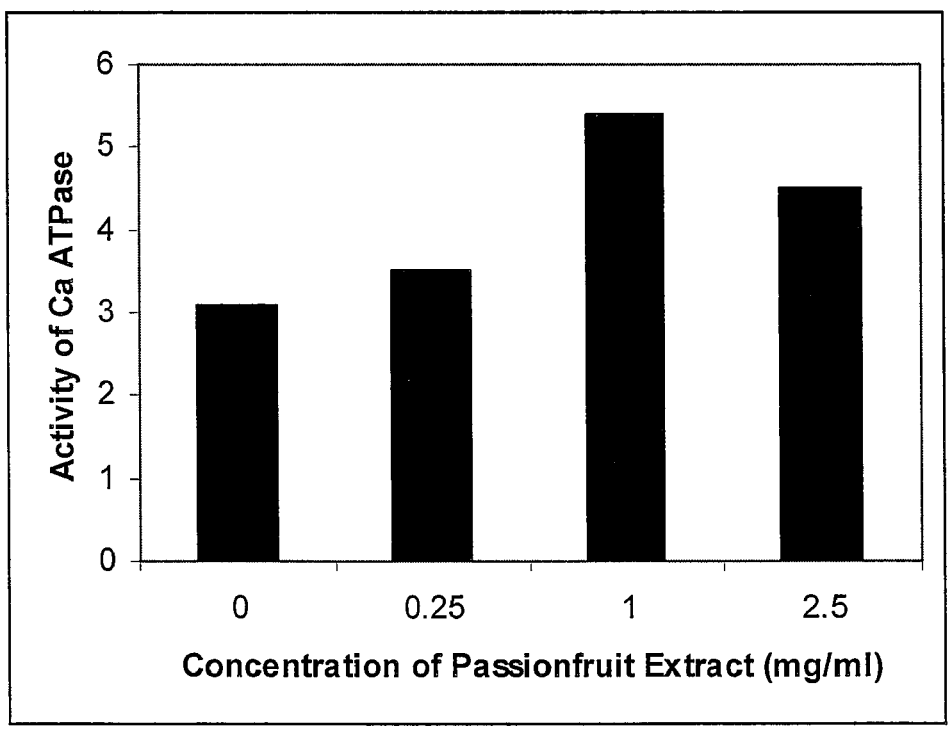

In vitro studies have also shown that the extract increases human red blood cell membrane-bound Na—K ATPase and Ca ATPase activity. RBC membrane-bound Na—K pump ATPase had much higher activity when cultured with the extract at either 0.25 mg/mL (increased by 102%), 1 mg/mL (increased by 107%), or 25 mg/mL (increased by 170%) than the control group (FIG. 4). The extract at concentrations of 1 mg/mL and 2.5 mg/mL increased membrane-bound Ca ATPase activity by 78% and 41% on average.

Figure 5B:
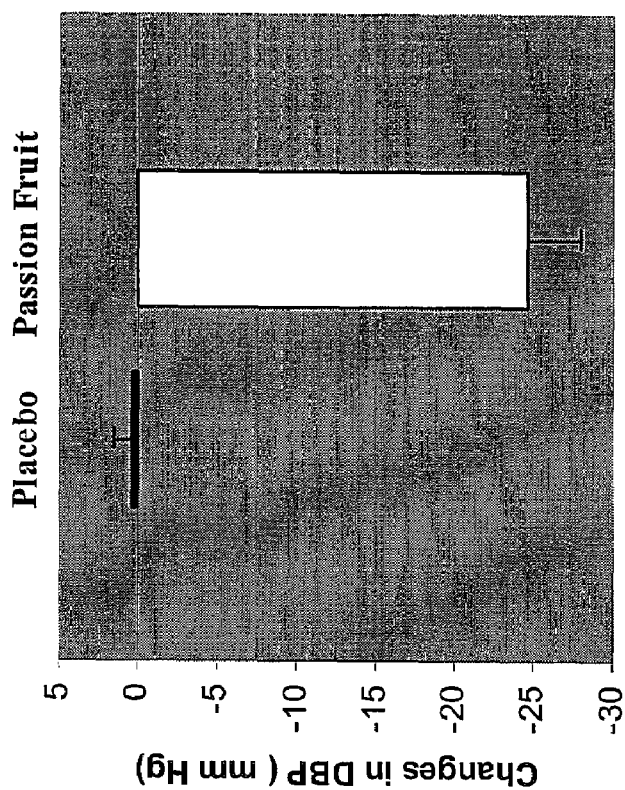
FIGS. 5*a* and 5*b* are diagrammatical representation of data showing the reduction in systolic blood pressure and diastolic blood pressure, respectively, in a group of humans administered the extract of passion fruit.
Figure 5A:
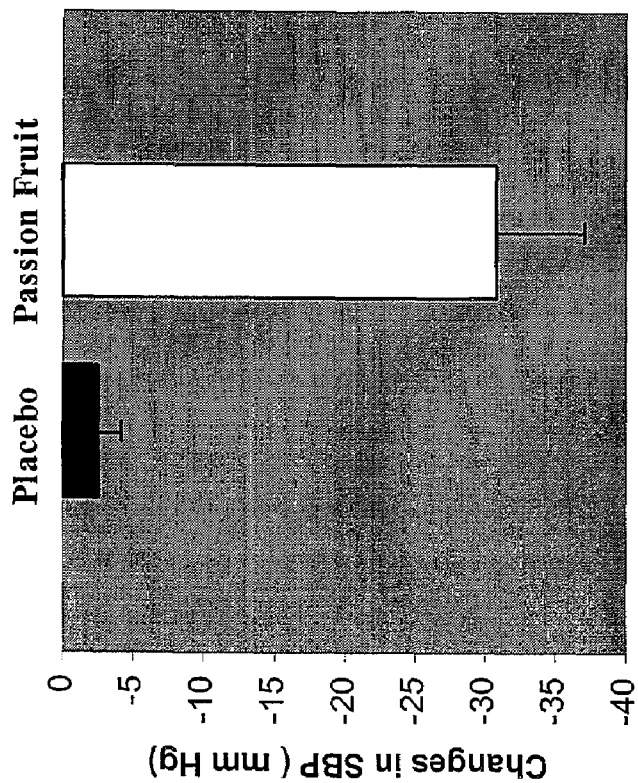

The applicants have also carried out human studies (FIG. 5). FIG. 5 shows the change in SBP (systolic blood pressure) and DBP (diastolic blood pressure) in hypertensive patients who received placebo or passion fruit extract (2 mg/lb/day, maximum 400 mg/day) for four weeks. Passion fruit extract or placebo pills were given in a randomized, double-blind, parallel group fashion to these patients. They had an average systolic blood pressure of 176.60±4.90 mm Hg (mean±SEM). Passion fruit treatment decreased systolic blood pressure significantly (p<0.001) to 145.67±4.44 mm Hg (mean±SEM) as compared to the placebo group. The data also demonstrated that passion fruit extract supplementation decreases diastolic blood pressure significantly (p<0.001) in hypertensive patients with an average diastolic blood pressure of 103.27±2.30 mm Hg (mean±SEM), to 78.67+2.78 mm Hg (mean±SEM). No patient in the study showed electrocardiographic changes after four weeks of therapy.

Because of the above-described activities, it is also expected that the passion fruit extract will benefit patients with inflammatory-related diseases, such as arthritis, asthma and allergies, as well as heart disease and hypertension. In addition, even though very large intakes or amounts of the extract were used in the studies described in this application, no toxicity of the extract was found in humans, rats, mice or cells in culture.

It will be appreciated by those skilled in the art that the extract may be administered to a patient by a variety of routes, including oral administration, or injection. The amount of extract to be administered will vary widely depending upon the patient and the nature and extent of the disorder to be treated. Typically, the extract is formulated as a composition which may be administered intravenously or by oral ingestion. The composition may be ingested or intravenously administered in any dosage levels and dosage frequencies suitable for lowering blood pressure, ameliorating the symptoms of asthma and/or osteoarthritis, and/or increasing immune function.

The composition of the invention may also be a food product, including, but not limited to, a nutritional supplement.

In the case of a pharmaceutical composition, the extract may be formulated into solid or liquid preparations, for example tablets, capsules, powders, solutions, suspensions and dispersions. Liquid forms include carriers such as water and ethanol, with or without other agents such as pharmaceutically acceptable surfactants or suspending agents.

The invention is further described with reference to the following examples. However, it is to be appreciated that the invention is not limited to these examples.

EXAMPLES

Example 1

Preparation of Passion fruit Extract

Passion fruits (*Passiflora edulis*) were cut into halves and the juicy pulp removed to give empty shells of passion fruit skin. The shells were chopped into small pieces less than 10 mm in length and placed in a container. Hot water (65-75° C.) was added to the container to immerse the chopped shells completely. The mixture was stirred occasionally during the first hour and then left to soak overnight. The mixture was filtered and the filtrate passed through a column of non-ionic polymeric resin to absorb phenolic and other organic compounds. Distilled water was passed through the column to wash out sugars and other polar components. The absorbed compounds were then eluted from the column with methanol and the eluant concentrated under reduced pressure to give a dark concentrate. The concentrate was freeze-dried to give the passion fruit extract as a dark red powder. While methanol was used as the eluting agent, ethanol, isopropyl alcohol, 1-propanol or acetone could also have been used.

Example 2

Determination of Components of Passion Fruit Extract

The components of the extract were determined by HPLC. Experiments were carried out on a Hewlett Packard 1100 instrument equipped with a DAD detector and a LiChrospher 100 RP-18 (um) column (125×4) held at 30° C. The solvent program started from 3.6% B (2% HOAc in acetonitrile) in solvent A (2% HOAc in water) up to 12% B in 20 min, to 20% in 30 min, and to 50% B in 45 min. Flow rate was set at mL/min and compounds were monitored by UV absorption set at 280 nm for phenolic acids, 350 nm for flavonoids and 520 nm for anthocyanins. The identity of the compounds was confirmed by comparison of retention times and UV/visible spectra with authentic materials.

Example 3

Red Blood Cell Membrane Preparation and ATPase Assay

Erythrocyte membranes were prepared as previously described (Farrance, M L., & Vincenzi, F F. (1977) *Biochim Biophys Acta* 471:49-58). Briefly, blood was taken from healthy humans. Red blood cells were washed with saline and lysed in a hypotonic imidazole buffer (pH 7.4, 20 mM, Sigma) with EGTA (100 mM, Sigma) and PMSF (10 mM, Sigma). Membranes were washed with imidazole buffer (20 mM) containing EGTA and PMSF, imidazole buffer containing EGTA, and only imidazole buffer each one time in sequence. The final wash was in 40 mM histidine-imidazole buffer (pH 7,4), and the membranes were stored in a refrigerator (4-8° C.) under nitrogen. Prior to assay, RBC membrane (0.75 mg/mL) was incubated for 30 minutes at 37° C. with 0, 0.25, 1, 2.5 mg/mL of passion fruit skin extract and enough saline to achieve a final volume of 1 mL. Following incubation and centrifugation, the supernatants were removed and the membrane was resuspended in saline up to 1 mL. Thereafter, membrane ATPase activities were measured simultaneously in multi-well plates. The typical assay mixture contained RBC membrane (75 μg/mL), 18 mM histidine-imidazole (pH 7.1, Sigma), 3 mM $MgCl_2$, 80 mM NaCl, 15 mM KCl, 0.2 mM $CaCl_2$, 0.1 mM EGTA, 0.1 mM Ouabain (Sigma) and 30 nM CaM (only for CaM-activated $Ca^{2+}$ pump, Sigma). After a 15 minute preincubation at 37° C., 5% SDS (Sigma) was added to the control groups. The enzymatic reaction was started with 3 mM ATP. After 60 minutes at 37° C., the-reaction was stopped with 5% SDS; and the inorganic phosphate released was measured with an ammonium molybdate/ascorbic acid mixture and absorption was measured at wave length 820 nm by Microplate Autoreader (Bio-Tek Instruments, EL311. USA). For additional accuracy, a BCA assay was performed to determine the final concentration of protein within the tubes at the end of each assay. Membrane (25 μl) from the above experiment, 25 μl $ddH_2O$ and 1 mL color reagent were added in a tube and then incubated for 30 mm at 37° C. Standard protein (Albumin, Sigma) at different concentrations was incubated in the meantime. After incubation, each tube was cooled to room temperature. Light absorbance was measured by spectrophotometer (Beckman Coulter, DU640) at X=562 nm. Protein concentration of the membrane was read from the standard curve.

The activity of ATPase was calculated by:

$$\text{Activity of } ATPase = \frac{N(P1) \times 0.2778 \times \text{protein concentration}}{\text{Initial protein concentration}(0.75 \text{ mg/mL})}$$

Example 4

Animals and Diets—SHR Studies

Spontaneously hypertensive rats (SHR), 6 weeks old, were kept at 22 to 20° C. and 50% humidity during the experiment. 24 SHRs were divided into 3 groups with 8 rats in each group. They were fed the following diets: basic diet, basic diet supplemented with the passion fruit extract at 50 mg/kg, or basic diet supplemented with the passion fruit extract at 110 mg/kg (Table 1). The amount of food intake, body weight and systolic blood pressure were recorded once a week. Systolic blood pressure was measured by tail cuff method (Softron, Co. Ltd, Tokyo, Japan). After 8 weeks of feeding, all the rats were sacrificed under anesthesia with Nembutal (0.1 mg/100 g body weight, Wako, Co. Ltd., Japan). Thymus, spleen, liver and heart were isolated and weighed. No toxicity was observed.

Example 5

Nitric Oxide Measurement

Measurement of nitric oxide was carried out as previously described (Rockett, K A., Awburn, M M., Cowden, W B. & Clark, J A. (1991) *Infect. Immun.* 59:3280-3). Nitric oxide is easily converted to nitrite. Nitrate was measured for nitric oxide. Dilutions of $NaNO_2$ (BDH; Wako, Co. Ltd., Japan) and test compounds were made in distilled water in 96-well, flat-bottom plates to a final volume of 50 ul. 20 microliters of $NH_4Cl$ borate buffer was added to all wells requiring analysis for nitric oxide/nitrite. 50 microliters of Griess reagent [1% sulfanilamide plus 0.1% N-(1-napthyl)ethylenenediamine dihydrochloride (Wako, Co. Ltd., Japan) in 2 M $H_2SO_4$] was then added to wells to be analyzed for nitric oxide/nitrite. The plate was read at 540 nm (test) and nitric oxide and nitrite concentrations were read directly from a nitrite standard curve.

Example 6

Human Hypertension Study

People with hypertension, 14 men aged 57.0±14.48 y (mean±SD) and 16 women aged 57.56±12.75 y (mean±SD), were included in the study. Patients had hypertension of stage 1 or 2 according to the guidelines of the Joint National Committee on Detection, Evaluation, and Treatment of High Blood Pressure. In repeated blood pressure measurements, they had systolic blood pressure (SBP) between 144 and 210 mm Hg and diastolic blood pressure (DBP) between 80 and 120 mm Hg. The exclusion criteria included those with renal or cardiac disease, taking oral contraceptives, use of tobacco and alcohol, or taking any vitamin supplements other than a single, daily multivitamin tablet. All of subjects included were taking antihypertensive combination therapy including diuretic, beta-blocker and ACE-inhibitor. More than one hundred were screened to select the thirty participants, none of which dropped out during the study.

At the beginning of the study, the passion fruit and placebo groups did not differ in mean blood pressure (SBP, 176.60±4.90 vs. 179.67±3.79 mm Hg and DBP, 103.27±2.30 vs. 104.33±2.06 mm Hg), age, sex, height, weight, heart rate, and pretreatment medication against hypertension or pattern of ECG.

The study was approved by Mashhad University's Human Subjects Committee. After providing informed consent and the one week withdrawal of any previous antihypertensive treatment except Triamterene-H in two subjects, eligible patients entered a four week, double-blind, placebo controlled, parallel group study. Patients were requested to attend clinic for follow-up every week during the study to assess side-effects. In addition, blood pressure and heart rate were measured. At the first visit, a complete medical history and a physical examination, including electrocardiogram, were carried out. Blood pressure was measured by a registered nurse, after the subject had been sitting for 10 min rest. Korotkoff phases I and V were taken as the systolic and diastolic blood pressures, respectively. Repeated readings were taken at 2 minute intervals for a total of 3 sitting measurements at each visit. Averages of repeated measurements at a given visit were recorded. At the second visit, blood pressure and heart rate were assessed again and patients were randomized to receive twice daily dosing of 2 mg/lb/day (maximum 400 mg/day) of a statistical formula of passion fruit pill or a similarly appearing placebo for 4 weeks. The data for week 1 and week 0 were combined as baseline values. In the last visit, for each patient an ECG was performed and the study drug was collected. All changes in concomitant medications and clinical adverse events, either volunteered or elicited by questioning, at baseline and follow-up visits were recorded, with none reported.

Compliance was evaluated by tablet counting. During the four-week period of treatment, all the subjects took 100% percent of the pills provided in a blinded fashion. All tests were two to four hours after the last consumption of pills.

Example 7

Isolation of Edulilic Acid from Passion Fruit Peel Extract

Passion fruit peel extract prepared according to Example 1 was dissolved in 50% aqueous ethanol and was treated on a Sephadex LH20 column and eluted with 50% aqueous ethanol. The chromatographic fractions were collected in 20 ml tubes with the aid of a fraction collector. Fractions were monitored by thin layer chromatography using cellulose TLC developed with 6% aqueous acetic acid and visualized under UV. Under this condition, the novel compound (Rf 0.8) co-eluted with the colored anthocyanins fraction (Rf 0.4-0.5). This fraction was collected and concentrated and re-chromatographed on a column of MCI GEL CHP 20P purchased from Mitsubishi Chemical Industries Ltd. Using 15% aqueous methanol as the eluating solvent. Fractions were collected and monitored by cellulose TLC developed with tertiary BuOH—AcOH—$H_2O$ (3/1/1 v/v). Fractions containing the novel compound (Rf 0.9 with this solvent) were collected and the solvent evaporated and the residue was freeze dried.

A high resolution electrospray ionization mass spectrum of edulilic acid was made on a MARINER Biospectrometry Workstation at the Victoria University of Wellington, New Zealand operating on the negative ion mode to give $(M-H)^{-1}$ peak at 301.09691 which corresponded to the molecular formulae of $C_{13}H_{18}O_8$. Various NMR studies (1H, 13C, COSY, HMQC, HMBC and NOSEY) and mass spectrometry were conducted on the edulilic acid. Table 1 contains data from the NMR studies.

TABLE 1

$^1$H and $^{13}$C NMR Spectral Assignment for Edulilic acid Recorded in $D_2O$

| C/H position | δ 13C | δ1H (HMQC) | HMBC |
|---|---|---|---|
| 1 | 29.1 | 2.70 (m) | C1, C2, C3, C4, C5, C6 |
| 2 | 31.8 | 2.37 (bs) | C3, C4 |
| 3 | 130.1 | 6.84 (d) | C1, C2, C4, C5 |
| 4 | 150.5 | 6.52 (d) | C1, C2, C3, C5 |
| 5 | 156.3 | — | |
| 6 | 132.7 | — | |
| 7 | 167.6 | — | |
| glucose | | | |
| C1' | 103.5 | 4.57 (d) | C2', C3', C6 |
| C2' | 76.4 | 3.30 (m) | C2', C2', C3' |
| C3' | 75.9 | 3.35 (m) | C4' |
| C4' | 73.7 | 3.32 (m) | C3', C4' |
| C5' | 69.5 | 3.30 (m) | C3', C4', C6' |
| C6' | 60.6 | 3.53 (dd), 3.67 (dd) | C5' |
| C7 (CO) | 167.6 | | |

On this basis the chemical structure of edulilic acid is as given below. The beta-linkage of the glucose residue is assigned due the large J-coupling magnitude (J=7.3 Hz) of the anomeric proton.

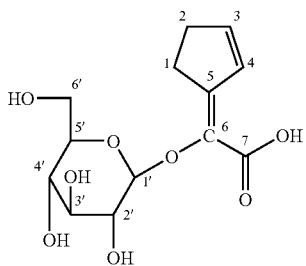

The drawing of the molecule was prepared using ACD/ChemSketch Software, which provided the IUPAC name (2E)-cyclopent-2-en-1-ylidene((3,4, 5-trihydroxy-6-(hydroxymethyl)tetrahydro-2H-pyran-2-yl)oxy)acetic acid. The compound has been identified throughout this specification as "edulilic acid", as having originally been discovered in the fruit of *Passiflora edulis*. The structure of edulilic acid depicted above is the E or trans isomer. Edulilic acid is expected to undergo cis/trans enolization to the Z or cis form and back. The electron shift can go from the C-2 protons through the acetic acid moiety, or from the acetic acid moiety and travel in the opposite direction to afford the same cis/trans result.

Figure 6A:
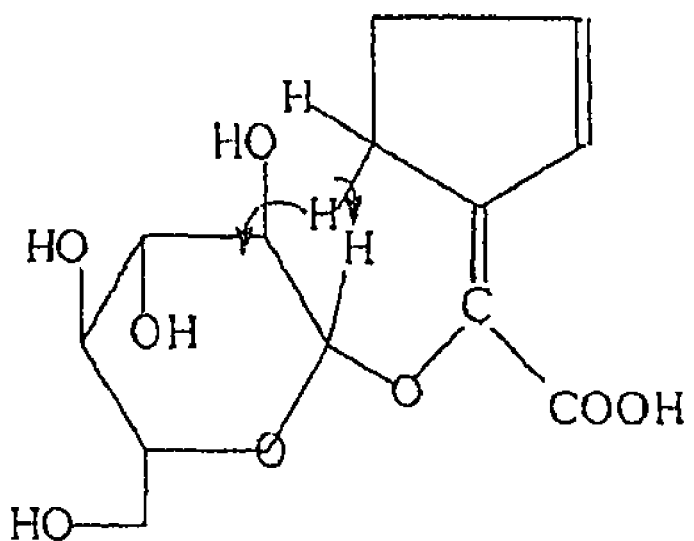
FIGS. 6a and 6b are drawings showing H-1 methylene proton interactions with H-1' and H-2' of the sugar moiety.
Figure 6B:
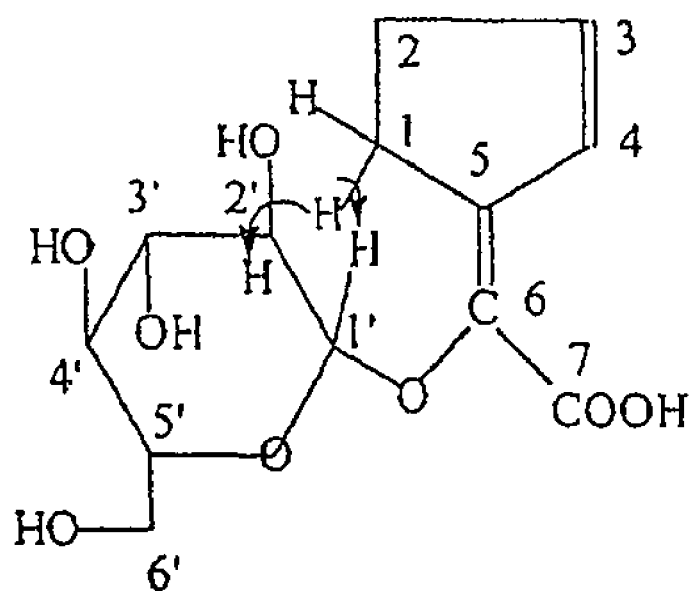

The NOESY spectrum of edulilic acid in D.sub.2O shows that there is some interaction of the sugar anomeric proton with the methylene protons on C-1 as numbered in the structure shown earlier (FIGS. 6a and 6b). This is only possible if the carboxylic acid moiety is on the double bond side of the cyclopentene ring. Further studies using a Dreiding model for edulilic acid show that the orientation of the sugar moiety that offer the least crowding to the cyclopentene ring indeed placed the anomeric proton in close proximity to the methylene protons on C-1.

Example 8

Detection of Edulilic Acid in the Pulp of Passion Fruit

Figure 7A:
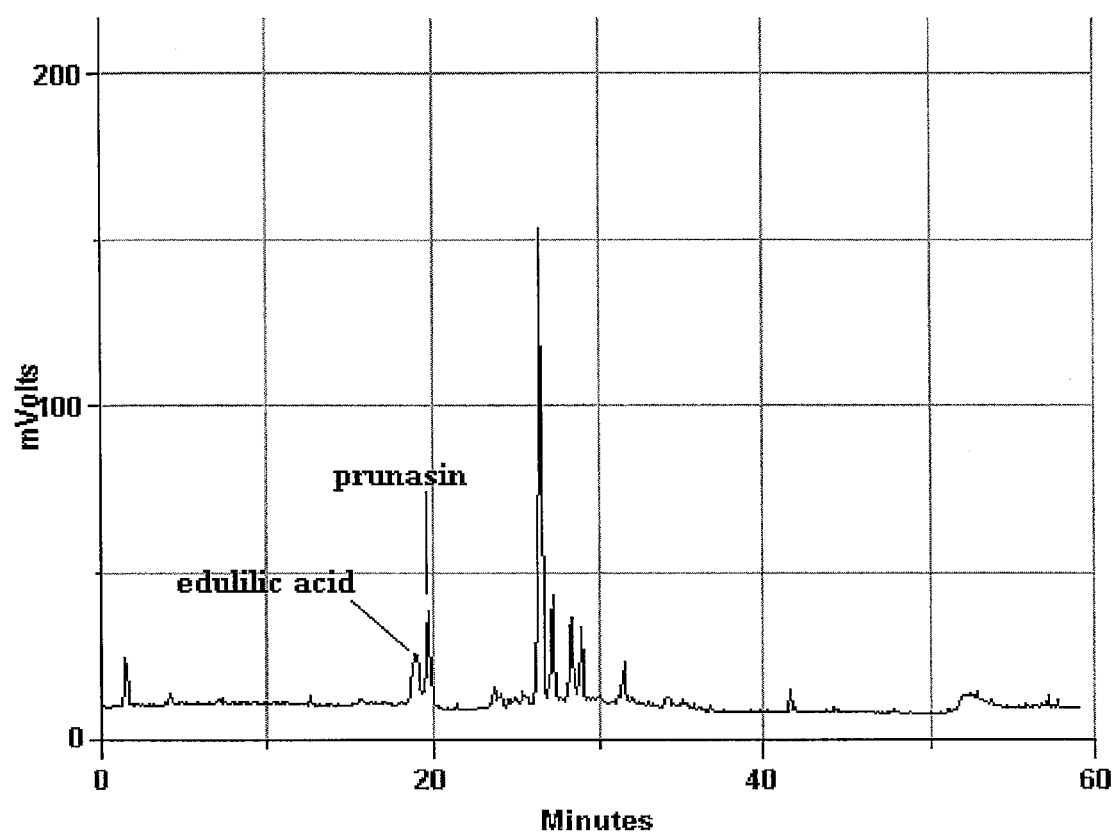
FIGS. 7a and 7b are HPLC-ELSD chromatograms of the extracts of passion fruit skin and pulp, respectively, obtained under identical conditions.
Figure 7B:
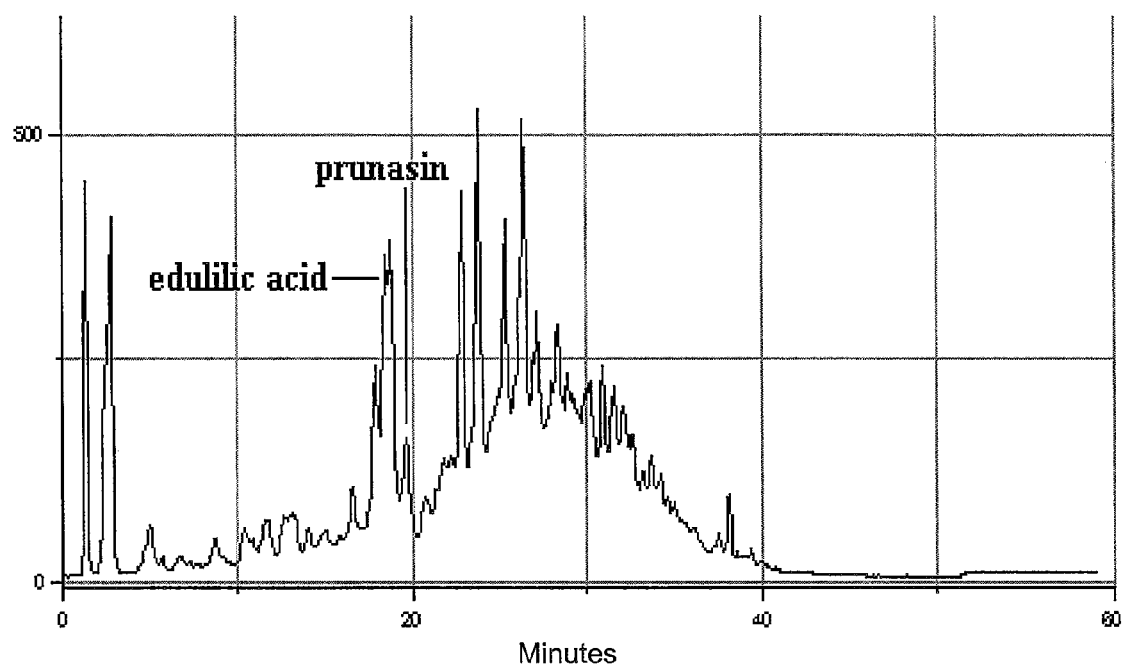

An aqueous extract of passion fruit pulp was prepared in a similar manner as described in Example 1 with respect to the skin, and its chemical profile was examined using HPLC. A different HPLC solvent programming using methanol instead of acetonitrile was used successfully to resolve the edulilic acid and prunasin peaks. Also, instead of UV detection Evaporative Light Scattering Detection (ELSD) was used for better detection of weak UV absorbing compounds such as prunasin. FIGS. 7a and 7b show the HPLC chromatograms of the extracts of the skin and pulp respectively obtained under such conditions. While the skin and pulp extracts were clearly distinguishable by their HPLC profile, it was also apparent that both edulilic acid and prunasin were present in both extracts.

Example 9

Human Asthma Study

Materials and Methods. Mashhad University's Human Subjects Committee approved the study. Patients fulfilling the American Thoracic Society criteria for asthma and meeting the entry criteria were included in the study. These included being asthmatic and aged 18-60 years of age, with baseline forced expiratory flow rate in one second (FEB1) values of 30-75% of predicted norm with an increase in FEV1 of more than 15% above pretreatment values after two puffs of a beta-adrenergic agonist. Volunteers with clinical evidence of chronic obstructive lung disease, renal, hepatic, cardiac problems, endocrine diseases, hypertension or pregnancy were excluded. They were permitted to take their usual medications except glucocorticoids, leukotiene antagonists, multivitamins, aspirin or any NSAIDS.

Study Design. After providing informed consent the eligible patients entered a four-week, double blind, placebo controlled, parallel group study. Comprehensive physical examination and baseline spirometric values were obtained at the enrollment visit. Spirometry was performed at each following visit. Severity of symptoms was rated on a 4 point scale: mild symptom of asthma: awareness of asthma symptoms and/or signs that were easily tolerated (score 1=needs only rescue medicine, score 2=needs daily medication), moderate symptoms and daily medications dependency (score 3), severe symptom and daily medication dependency (score 4). People with asthma were included in the study. The exclusion criteria included those with renal or cardiac disease, taking oral contraceptives, use of tobacco and alcohol, or taking any vitamin supplements other than a single, daily multivitamin tablet. More than one hundred were screened to select the participants.

Patients were requested to attend the clinic for follow-up every week during the study to assess side effects. At the first visit, a complete medical history and physical examination, including skin prick and liver function tests were carried out. A registered nurse measured blood pressure, after the subject had been sitting for 10 min rest. At the second visit, inhaled and expired air, and shortness of breath were assessed again and patients were randomized to receive the PFP extract pill 150 mg/day or a similar-appearing placebo pill for 4 weeks. Pills were taken in the morning. The data for week −1 and week 0 were combined as baseline values. On the last visit for each patient, an ECG was performed and the study extract was collected. All changes in concomitant medications and clinical adverse events, either volunteered or elicited by questioning, at baseline and follow-up visits were recorded, with none reported. Compliance was evaluated by tablet counting. During the four-week period of treatment, all the subjects took 95% percent of the pills provided in a blinded fashion. All tests were two to four hours after the last consumption of pills.

Statistics. The primary efficacy variables were changes from baseline in asthma symptom scores and pulmonary function tests ($FEV^1$% predicted, $FEV^1/FVC$). Secondary efficacy variables included serum levels of Th1 and Th2 cytokines (IL-2 and IL-4). The effects of the PFP extract therapy on each subject and for each parameter were assessed with the use of a paired two-tailed t test. A probability of less than 0.05 was considered significant and was confirmed with a nonparametric test, the Friedman Measures Analysis of Variance on Ranks. That test showed whether at least one of the tested groups differed from the other groups. The statistical significant difference between experimental groups was analyzed by Generalized estimate equations method (using software Stata) and Student's t test (using software SPSS).

Results. The demographic characteristics included 13 female and 6 male given placebo and 16 female and 8 male subjects taking PFP extract pills. Of the 44 patients enrolled, 42 completed the study with 2 withdrawing. Their average age was 34 years.

In addition height, weight, and pretreatment medication against asthma did not differ significantly (data not shown). The PFP extract or placebo pills were given in a randomized, double blind, parallel group fashion for four weeks to asthma patients. They had an average of 130 of 70 mm Hg (mean+/− 120/70).

Figure 8:
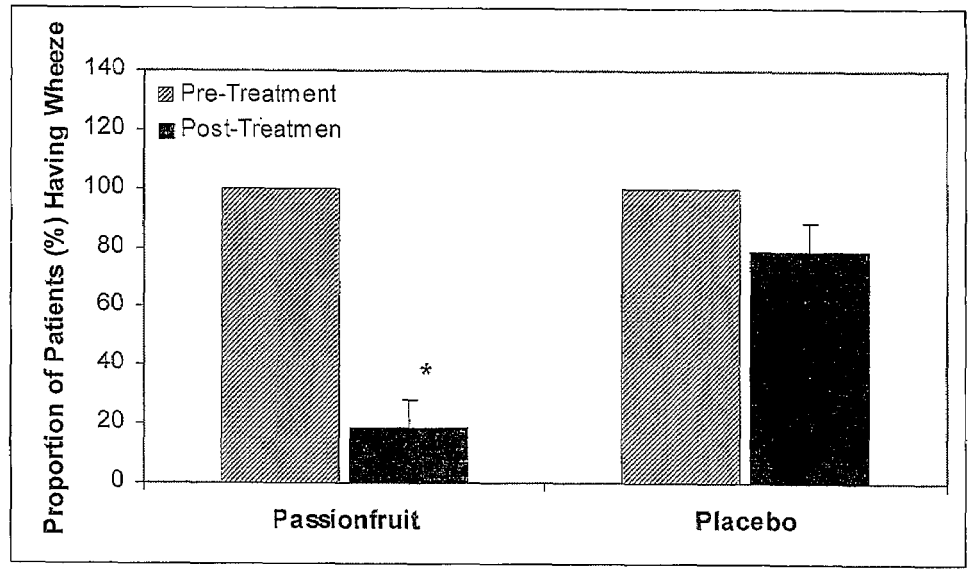
FIG. 8 is a graphical representation of the effect of passion fruit extract on the proportion of patients having wheeze, an asthma symptom, before and after treatment; asthmatic patients received placebo or passion fruit extract (150 mg/day) for four weeks; data are shown as mean±SEM. *P<0.05 as compared with placebo group.
Figure 9:
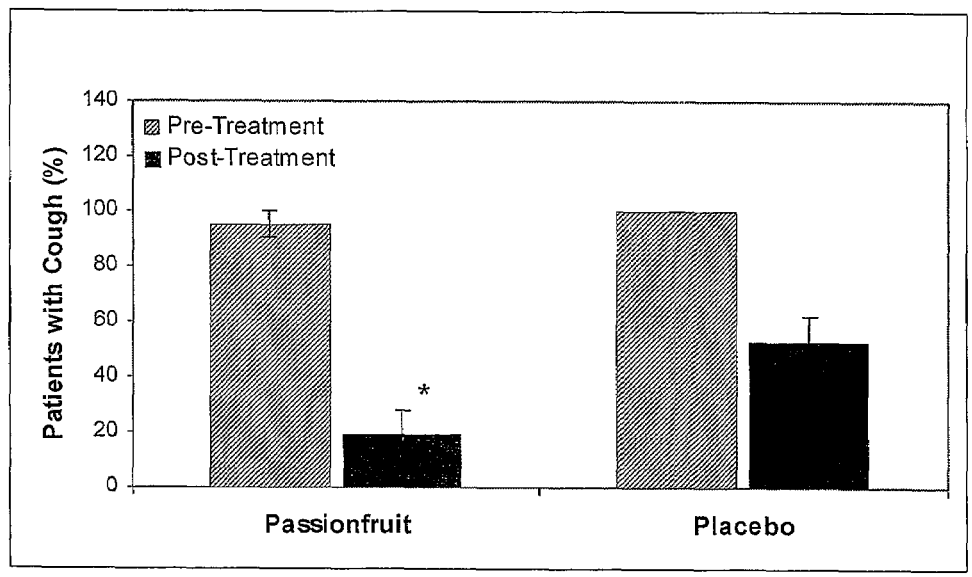
FIG. 9 is a graphical representation of the effect of passion fruit extract on the proportion of patients having cough, an asthma symptom, before and after treatment; asthmatic patients received placebo or PFP extract (150 mg/day) for four weeks; data are shown as mean±SEM. *P<0.001 as compared with placebo group.
Figure 10:
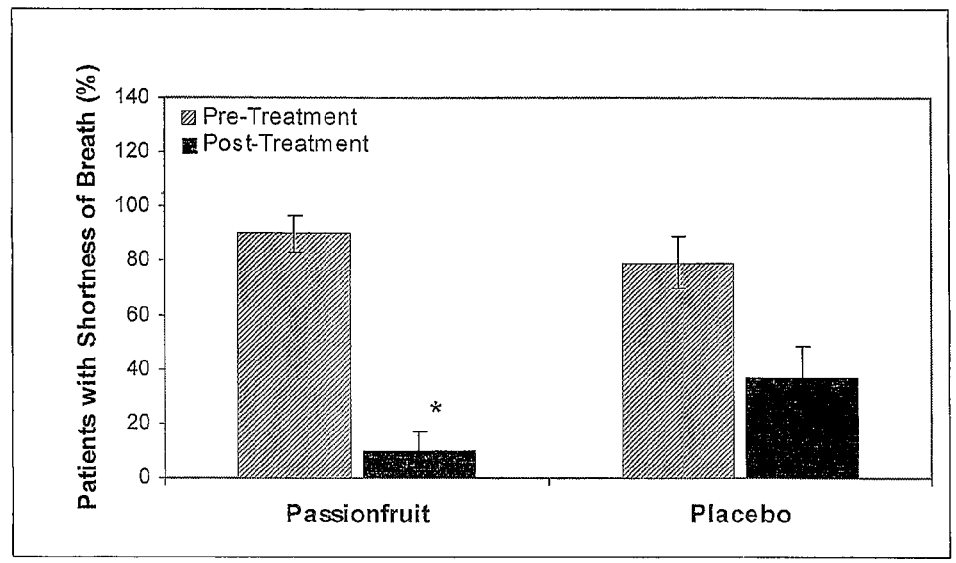
FIG. 10 is a graphical representation of the effect of passion fruit extract on the proportion of patients having shortness of breath, an asthma symptom, before and after treatment; asthmatic patients received placebo or PFP extract (150 mg/day) for four weeks; data are shown as mean±SEM. *P<0.005 as compared with placebo group.
Figure 11:
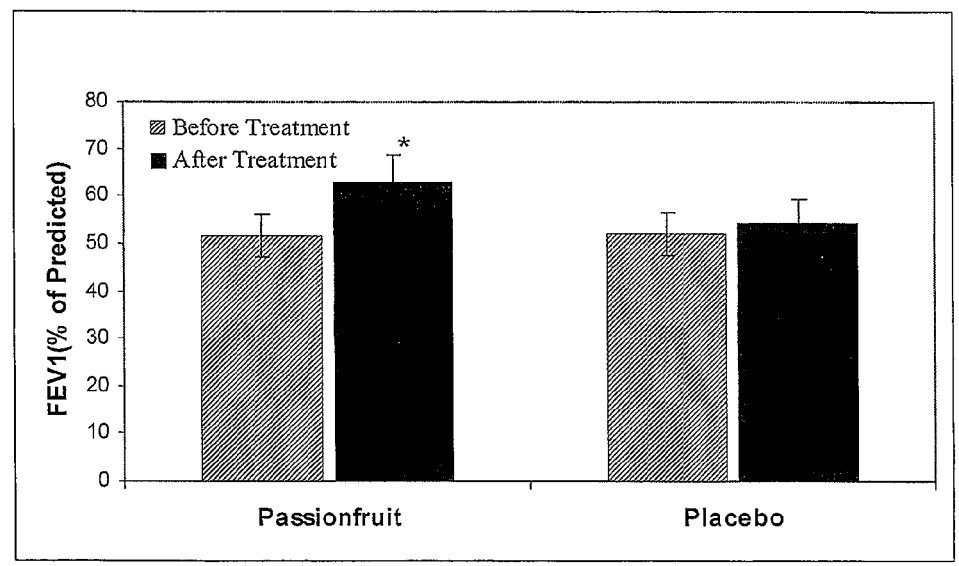
FIG. 11 is a graphical representation of the effect of passion fruit extract on forced expiratory volume in the first second (percent of predicted), before and after treatment in asthmatic patients who received placebo or passion fruit extract (150 mg/day) for four weeks; data are shown as mean±SEM.
Figure 12:
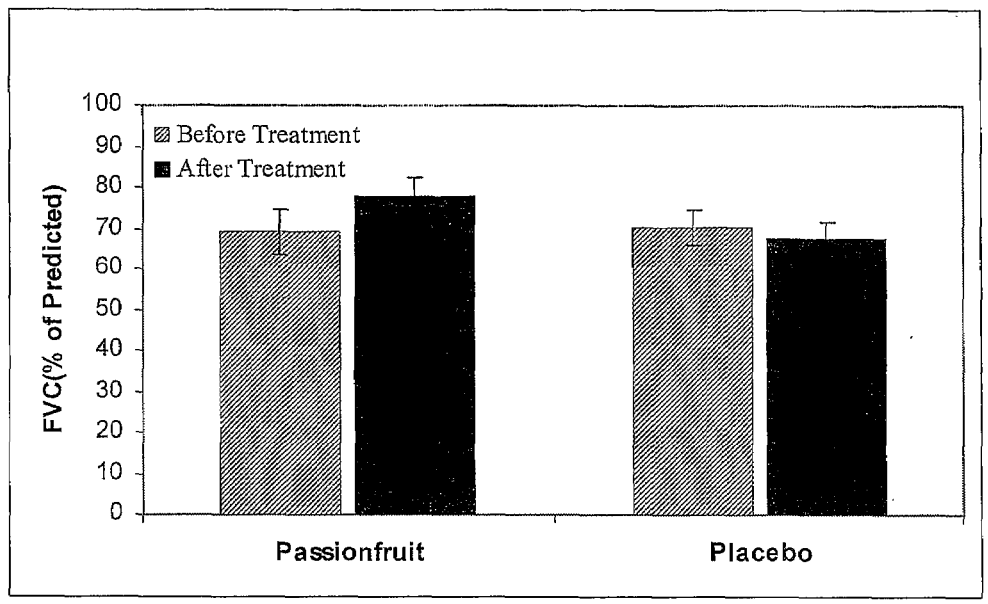
FIG. 12 is a graphical representation of the effect of passion fruit extract on forced vital capacity (percent of predicted), before and after treatment in asthmatic patients who received placebo or passion fruit extract (150 mg/day) for four weeks; data are shown as mean±SEM.
Figure 13:
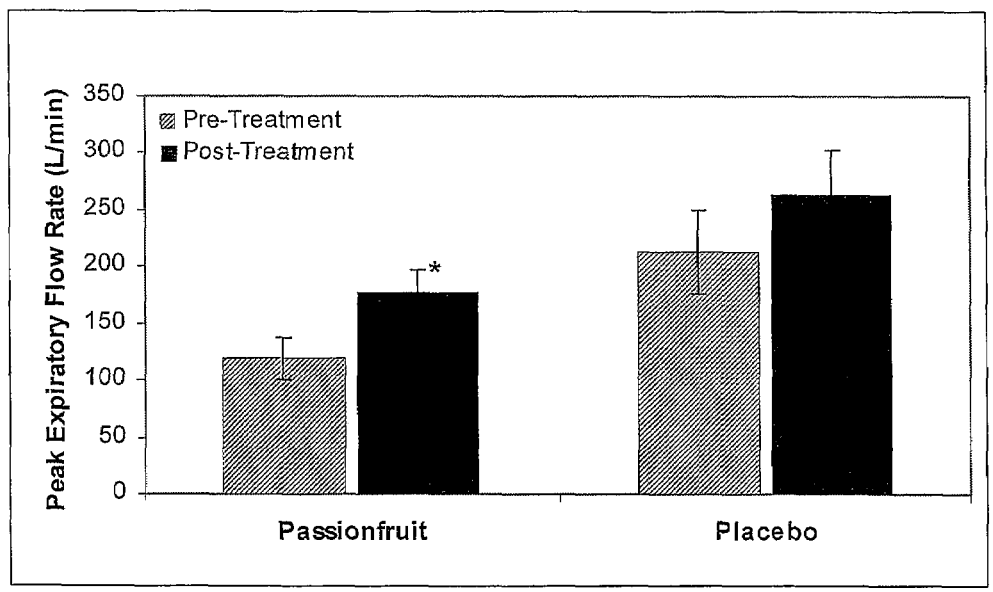
FIG. 13 is a graphical representation of the effect of passion fruit extract on peak expiratory flow rate (L/min), before and after treatment in asthmatic patients who received placebo or passion fruit extract (150 mg/day) for four weeks; data are shown as mean±SEM. *P<0.05 as compared with placebo group.

Of the patients having wheeze as a clinical symptom only 20% still had it after treatment with PFP while 80% in the placebo group (FIG. 8). Similarly those with cough declined 85% during PFP treatment while cough was reduced only 45% in placebo (FIG. 9). Shortness of breath was found in 90% of patients before PFP treatment while it was present in only 10% afterwards (FIG. 10). In placebo treated subject 80% had shortness of breath before treatment and 38% afterwards, a smaller, non-significant decline (FIG. 10). The $FEV^1$ increased in PFP and placebo treated subjects (FIG. 11). However the increase was statistically significant only in the PFP group. Forced Vital Capacity increased in the PFP treated subjects and declined in the placebo treated subjects (FIG. 12). Peak expiratory flow increased significantly due to PFP treatment while placebo had no effect (FIG. 13).

Discussion. The results of this pilot study indicate that the PFP extract may be a valuable dietary supplement ingredient in the management of chronic asthma symptoms. The principal findings of the present study are (A) the PFP extract produced clinically and statistically significant reductions in symptoms of asthma after four weeks of supplementation in patients and (B) increased forced expired air and peak expiratory air flow. These observations show that PFP and its strong antioxidant properties had anti-inflammatory actions, which support recent studies where PFP reduced severe hypertension in people and animals. As the subjects only received the PFP extract for 4 weeks, longer treatment might enhance its beneficial effects.

Example 10

Human Osteoarthritis Study

Materials and Methods. Mashhad University's Human Subjects Committee approved the study. Patients fulfilling the American College of Rheumatology criteria for primary knee osteoarthritis (grade 1 and grade 2) and meeting the entry criteria were included in the study. These included being between 25 and 65 years old, having a "WOMAC" (the Western Ontario and McMaster Universities Osteoarthritis Index) pain subscale index of at least 20 at the baseline, and having intermittent or constant pain in the target knee for at least 50% of the time in last three months that required medical treatment in the form of NSAIDs or selective COX-2 inhibitors on most days. Exclusion criteria were the existence of secondary osteoarthritis due to a known disorder, arthroscopy, surgery, or a joint injection of the target knee within the previous six months, prior history of knee joint replacement, having any serious systemic disease; or having any other chronic inflammatory disease.

Study Design. After providing informed consent the eligible patients entered a one-month, randomized, double blind, placebo controlled, parallel group study. Comprehensive physical and x-ray evaluation were performed at the initial visit. In the second (baseline) visit, patients completed the WOMAC form and were allocated to receive either PFP extract (50 mg, three time a day) or matched placebo. The baseline characteristics of the study subjects are set out in Table 2.

TABLE 2

Baseline Characteristics of Osteoarthritis Study Subjects

| Variable | PFP Group | Placebo Group |
| --- | --- | --- |
| Number | 17 | 16 |
| Age, year (mean ± SD) | 55.0 ± 14.1 | 62.4 ± 7.9 |
| Gender, Male/Female | 5/12 | 4/12 |
| WOMAC Score (mean ± SEM) | | |
| Pain | 22.6 ± 1.7 | 33.7 ± 1.6 |
| Stiffness | 11.1 ± 1.0 | 14.4 ± 0.7 |
| Physical Function | 86.6 ± 4.1 | 129.2 ± 5.9 |
| Composite | 120.3 ± 5.7 | 177.3 ± 7.7 |

At final visit, which was one month after the baseline visit, the effect of the treatment on joint pain, stiffness, and limitation of physical function were evaluated using the WOMAC index Statistics. Statistical analyses were performed with GraphPad Prism 4.02 and JMP 6.0.0. Values represent mean±SEM unless otherwise noted. The change from baseline between the PFP group and the placebo group were compared using Student's t-test. Comparable nonparametric tests (Mann-Whitney) were substituted when tests for normality and equal variance failed.

Figure 14:
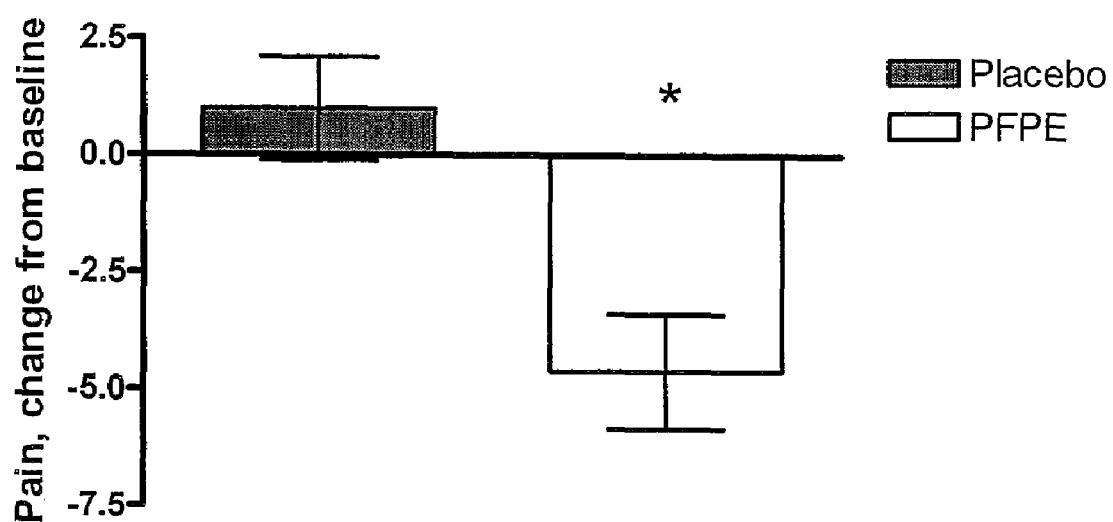
FIG. 14 is a graphical representation of the effect of passion fruit extract on the WOMAC pain subscale before and after treatment in osteoarthritis patients who received placebo or passion fruit extract (150 mg/day) for one month.
Figure 15:
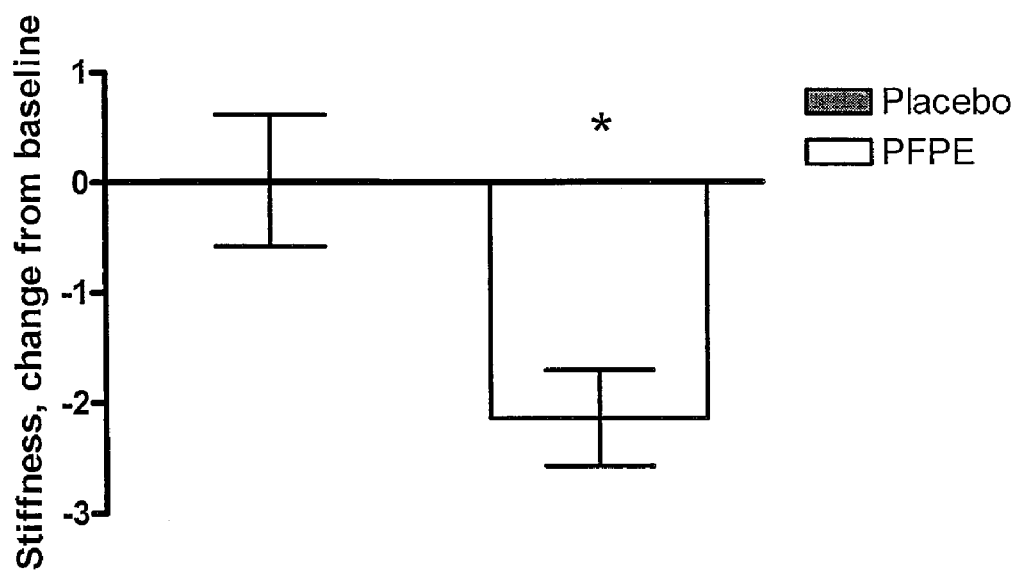
FIG. 15 is a graphical representation of the effect of passion fruit extract on the WOMAC stiffness subscale before and after treatment in osteoarthritis patients who received placebo or passion fruit extract (150 mg/day) for one month.
Figure 16:
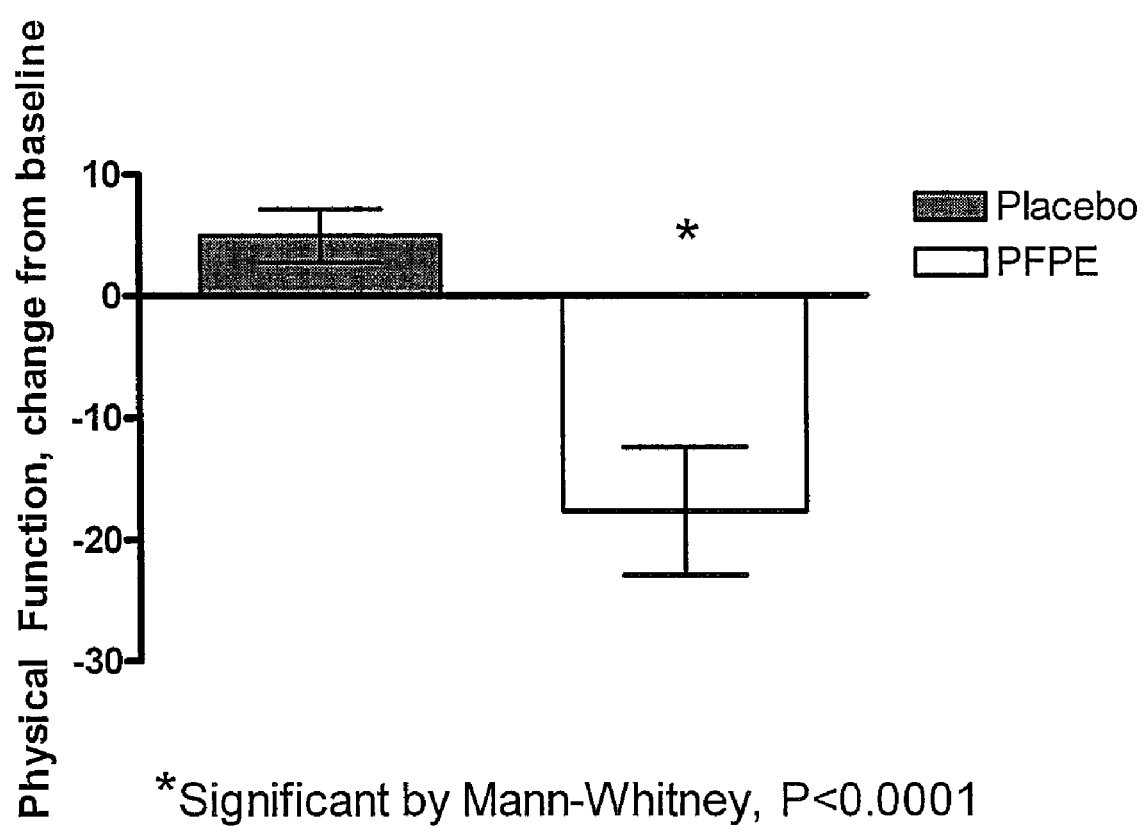
FIG. 16 is a graphical representation of the effect of passion fruit extract on the WOMAC physical function subscale before and after treatment in osteoarthritis patients who received placebo or passion fruit extract (150 mg/day) for one month.
Figure 17:
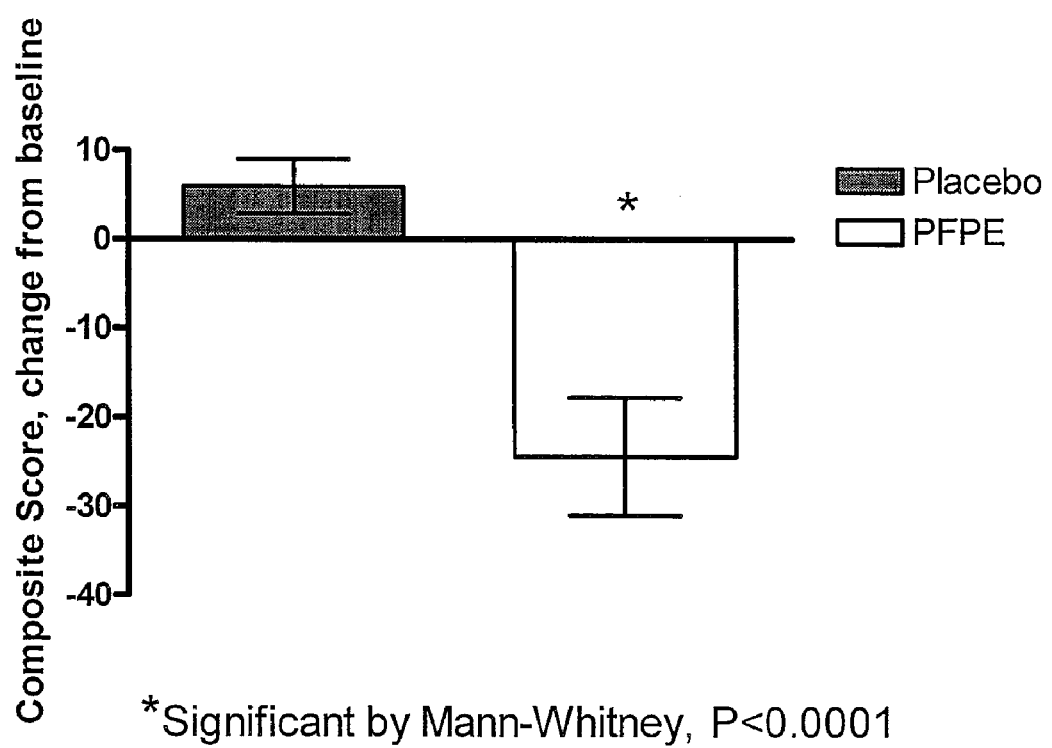
FIG. 17 is a graphical representation of the effect of passion fruit extract on the WOMAC composite score before and after treatment in osteoarthritis patients who received placebo or passion fruit extract (150 mg/day) for one month.

Results. The PFP extract (total of 150 mg/d of extract) or placebo were given to patients for four weeks and compliance assessed by counting pills at each visit. The WOMAC index values were recorded, averaged, change from baseline calculated, and statistically evaluated for each of the testing parameters including pain, stiffness, physical function, and composite score. FIG. 14 shows that there was a statistically significant reduction in pain from baseline in the PFP group compared to the placebo group (p=0.009) after four weeks of supplementation. FIG. 15 shows that there was a statistically significant reduction in stiffness from baseline in the PFP group compared to the placebo group (p<0.0001) after four weeks of supplementation. FIG. 16 shows that there was a statistically significant decrease in physical function from baseline in the PFP group compared to the placebo group (p<0.0001) after four weeks of supplementation. A reduction in the WOMAC physical function subscale value indicates an improvement in physical function. There was also a statistically significant decrease in the composite WOMAC score (pain, stiffness, and physical function combined) from baseline in the PFP group compared to the placebo group (FIG. 17, p<0.0001) after four weeks supplementation.

Discussion. The osteoarthritis pilot study data show that passion fruit extract has activity in decreasing the effects of osteoarthritis in humans. The WOMAC index is a validated measure of osteoarthritis parameters and is well respected in the medical profession. The activity of passion fruit extract on symptoms related to osteoarthritis most likely is due to its anti-inflammatory and antioxidant effects. Passion fruit extract could be administered as a dietary supplement ingredient for the osteoarthritic patient who may desire an alternative therapy to NSAIDS or who may want to supplement their diet to promote overall health.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of ameliorating the symptoms of asthma or osteoarthritis in a mammal in need thereof, comprising administering to the mammal an effective amount of a water extract of passion fruit peel to ameliorate the symptoms of asthma or osteoarthritis.

2. A method as defined in claim 1, wherein the amount is between about 0.1 and 5 mg per day per pound of body weight of the mammal.

3. A method as defined in claim 1, wherein the mammal is human.

4. A method as defined in claim 3, wherein the amount is between about 2 mg and about 1000 mg per day.

5. A method as defined in claim 2, wherein the symptoms are selected from the group consisting of wheeze, cough, shortness of breath, reduced forced expiratory volume, reduced forced vital capacity, and reduced peak expiratory flow rate.

6. A method as defined in claim 5, wherein the amount is between about 0.1 and 5 mg per day per pound of body weight of the mammal.

7. A method as defined in claim 5, wherein the mammal is human.

8. A method as defined in claim 7, wherein the amount is between about 2 mg and about 1000 mg per day.

9. A method as defined in claim 1, wherein the symptoms are selected from the group consisting of pain, stiffness, and physical function.

\* \* \* \* \*